United States Patent [19]
Martin et al.

[11] Patent Number: 5,500,411
[45] Date of Patent: Mar. 19, 1996

[54] METHOD FOR TREATING THROMBOEMBOLIC CONDITIONS BY INHIBITING REOCCLUSION VIA THE USE OF MULTIPLE BOLUS ADMINISTRATION OF THROMBOLYTICALLY ACTIVE PROTEINS

[75] Inventors: Ulrich Martin, Mannheim; Reinhard Koenig, Grunstadt, both of Germany

[73] Assignee: Boehringer Mannheim GmbH, Mannheim, Germany

[21] Appl. No.: 137,116

[22] PCT Filed: Apr. 15, 1992

[86] PCT No.: PCT/EP92/00851

§ 371 Date: Jun. 30, 1994

§ 102(e) Date: Jun. 30, 1994

[87] PCT Pub. No.: WO92/18157

PCT Pub. Date: Oct. 29, 1992

[30] Foreign Application Priority Data

Apr. 16, 1991 [DE] Germany ............... 41 12 398.0
Jul. 18, 1991 [DE] Germany ............... 41 23 845.1

[51] Int. Cl.⁶ ............... A61K 38/00; A61K 38/48
[52] U.S. Cl. ............... 514/12; 435/212; 435/215; 435/216; 435/226; 424/94.63; 424/94.64
[58] Field of Search ............... 424/94.63, 94.64; 514/12; 435/212, 215, 216, 226

[56] References Cited

U.S. PATENT DOCUMENTS

| | | | |
|---|---|---|---|
| 4,970,159 | 11/1990 | Dodd | 435/226 |
| 4,980,165 | 12/1990 | Isaacs et al. | 424/94.64 |
| 5,084,274 | 1/1992 | Griffin et al. | 424/94.64 |
| 5,223,256 | 6/1993 | Stern et al. | 424/94.63 |
| 5,234,686 | 8/1993 | Dodd | 424/94.64 |
| 5,242,688 | 9/1993 | Burck et al. | 424/94.64 |
| 5,350,578 | 9/1994 | Griffin et al. | 424/94.64 |
| 5,352,453 | 10/1994 | Kohnert et al. | 424/94.64 |
| 5,366,730 | 11/1994 | Kohnert et al. | 424/94.64 |

OTHER PUBLICATIONS

Klabunde et al "Thrombosis Res." 58:511–517 (1990).

*Primary Examiner*—Herbert J. Lilling
*Attorney, Agent, or Firm*—Felfe & Lynch

[57] ABSTRACT

Discussed are therapeutic approaches to the treatment of thrombolic conditions. The therapies use thrombolytically active proteins which inhibit reocclusion in the subject. The proteins are administered in two or more boli.

6 Claims, 5 Drawing Sheets

METHOD FOR TREATING THROMBOEMBOLIC CONDITIONS BY INHIBITING REOCCLUSION VIA THE USE OF MULTIPLE BOLUS ADMINISTRATION OF THROMBOLYTICALLY ACTIVE PROTEINS

FIELD OF THE INVENTION

The subject of the present invention is the use of thrombolytically active proteins for treating thromboembolic conditions, via multiple bolus administration.

The methodology employed inhibits the reocclusion rate in the subject so treated. Preferably, the thrombolytically active protein has a half life longer than that of recombinant t-PA

BACKGROUND AND PRIOR ART

Thrombolytic therapy of myocardial infarction is an effective, medically well tested and proved therapy for the removal of occlusive thrombi in the coronary arteries of the heart. Recombinant human t-PA (tissue-type plasminogen activator) produced by DNA technology is used in accordance with U.S. Pat. No. 4,766,075 has proven to be effective for the dissolution of coronary thrombi (Verstraete et al., Lancet II, 1985; 965–969). By early lysis therapy of the myocardial infarction the residual heart function after myocardial infarction can be improved in comparison with other therapies (Armstrong et al., J. Hm. Coll. Cardiol., 1989; 13: 1469–1476) and a higher survival rate can be achieved in comparison with other therapies (Wilcox et al., Lancet II, 1988; 525–539).

Large thrombolysis studies with, in all, several thousand patients show that rapid induction of thrombolysis with early reperfusion of the myocardial tissue leads to rescue of myocardial tissue and thus to an increase of survival rate (GISSI study group, Lancet I, 1986; 397–401). For this reason, it is necessary to induce thrombolytic therapy at a point of time at which the tissue lying behind the coronary occlusion is not yet irreversibly damaged.

In principle, in the case of the treatment of a coronary occlusion, the problem exists of avoiding reocclusion of the infarcted blood vessel after successful initial thrombolysis. This disadvantageous effect has been observed for recombinant t-PA (e.g., Alteplase) (Chesebro et al., Circulation, 1987; 76: 142–154). The reocclusion of the infarcted blood vessel leads to increased morbidity and mortality. For the prevention of reocclusions, substances are used of differing pharmacological working principles, such as heparin (Bleich et al., Am. J. Cardiol., 1990; 66: 1412–1417) and acetylsalicylic acid (Hsia et al., N. Engl. J. Med. 1990: 323: 1433–1437). The prolonged infusion of recombinant t-PA (Alteplase) is also said to prevent the reocclusion of the infarct blood vessel due to a longer period of thrombolysis (Gold et al., Circulation, 1986: 73: 347–352; Verstraete et al., Am. J. Cardiol. 1987; 60: 231–237; Johns et al., Circulation, 1988; 78: 546–556). However, after ending of the infusion, the appearance of reocclusions is frequently observed.

Human tissue plasminogen activator, produced by recombinant DNA technology ("rt-PA") has already been administered as double or multiple bolus to a few patients in the scope of clinical preliminary investigations. Admittedly, high dissolution rates of the thrombi were found up to 90 minutes after the administration of the first bolus but, because of the high doses, extensive, systemic plasminogen activation with subsequent almost complete reduction of fibrinogen was observed (only 15.5 to 5.2% of the initial value) (J. Am. Coll. Cardiol. 1991 (17(2), 152A). Undesired reduction of fibrinogen levels represents a disadvantage in that during emergency operations, since there is a high tendency to haemorrhage intensive supervision of the patient is necessary. Further, in the case of double and triple bolus administration of rt-PA, tendency to reocclude was observed in the blood vessels (Circulation, 1990, 82(4), Suppl. III, 538, abstract 2137; Br. J. Haematol. 1991, 77, Suppl. 1, 47, abstract P080). A study was also carried out for Alteplase in which multiple bolus administration was investigated in more detail (Coronary Artery Disease, 1990, 1(1), 83–88). The study concluded that single bolus administration was preferred.

Because of the above-mentioned disadvantageous effects, administration of rt-PA in the form of a double or multiple bolus has bound no practical use. Furthermore, the bolus administration of rt-PA has been regarded as being inexpedient from the fact that the half life of rt-PA is relatively short and only amounts to 3–6 minutes (Garabedian et al., J. Am. Coll. Cardiol. 1987; 9: 599–607). This means that, to ensure thrombolytic efficacy, relatively long-lasting infusion is necessary for the maintenance of effective plasma levels. However, in emergency situations the long-lasting infusion of r-tPA (30 minutes to 6 hours) represents a distinct treatment disadvantage. Furthermore, this leads to increased risk of haemorrhages (Marder and Sherry, N. Engl. J. Med. 1988; 318: 1512–1520).

Surprisingly, it has now been found that thrombolytically active proteins, preferably those with a half life longer than that of rt-PA can be used successfully in the treatment of coronary occlusions, when the proteins used are administered in the form of a fractionated administration of two or more bolus injections. In this way, rapid and simple administration of thrombolytically active proteins for the effective treatment of thromboembolic diseases by, e.g., inhibiting reocclusion rate, is made possible.

DETAILED DESCRIPTION OF PREFERRED EMBODIMENTS

Figure 1:
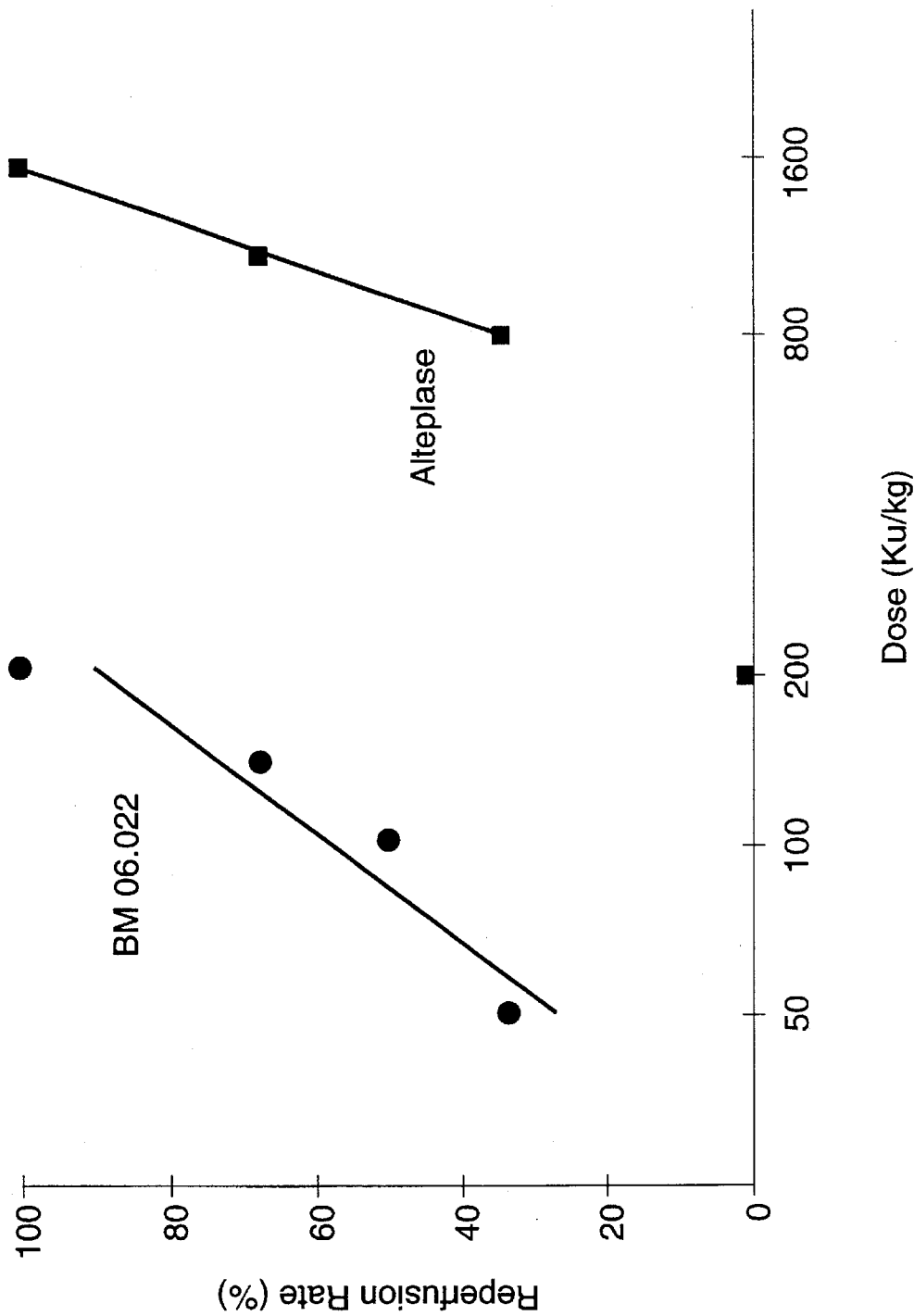
FIG. 1 compares the thrombolytic dose-effect range of thrombolytically active protein BM 06.022 and r-tPA (Alteplase), following an intravenous injection extending over one minute, in a dog model where the animals have coronary thrombosis. Reperfusion rate (%) is given as the percent of reperfused dogs with a dosage group (each group contains 6 dogs). The curves were produced using semi-logarithmic regression analysis.

In the meantime of the present invention, the term "fractionated administration" means the administration of a therapeutically effective amount of a thrombolytically active protein in two or more partial amounts in the form of a double or multiple bolus, "therapeutically effective amount" referring to sufficient protein to inhibit reocclusion.

Bolus administration is an intravenous rapid injection and is, therefore, especially advantageous because the time from the beginning of the clinical symptoms up to treatment and, also the time from the commencement of treatment up to the dissolving of the coronary thrombus is shortened. Thus, more myocardial tissue can be rescued from irreversible destruction. The double or multiple bolus administration according to the invention brings about a higher thrombolytic potency of the thrombolytically active protein use. In this way, it is possible to reduce dosages as compared to rt-PA. Surprisingly, after bolus injection, more rapid reperfusion as compared to administration in the form of an infusion is found. Furthermore, double or multiple bolus administration brings about a significant prolongation of the cumulative patency time (sum of the time intervals after reperfusion in which coronary blood flow is present), as well as a distinct increase of coronary blood flow, as well as increased stability at a relatively high level for a longer period of time after the administration. Furthermore, double or multiple bolus injection has the surprising advantage of a smaller decrease of plasma fibrinogen as compared to single bolus injection. However, these advantageous properties are not achieved with administration of the corresponding total amount of the thrombolytically active protein by single bolus injection.

Thromboembolic conditions in the meaning of the present invention include, but are not limited to, those diseases which are attributable to myocardial infarction or to reocclusion of the coronary arteries. Reocclusions occur quite frequently as a result of the use of thrombolytic agents for the treatment of heart infarcts. The case of myocardial infarctions is the formation of a thrombus in the coronary arteries. This thrombus consists of a combination of fibrin and thrombocytes. The primary aim in treatment of heart infarcts is the rapid dissolution of this thrombus and the recreation of the blood flow (reperfusion). Successful therapy must dissolve the thrombus as quickly as possible and prevent its reformation (reocclusion). Double or multiple bolus administration in accordance with the present invention is especially advantageous for the treatment of brain stroke.

Pharmaceutical packaging units prepared for use in the invention consists of a form of administration which contains the thrombolytically active protein instructions, for example in the form of a package leaflet prescribed for medicaments, from which it follows that the administration of a therapeutically effective amount of the thrombolytically active protein advantageously takes place by double or multiple bolus administration. The information regarding the manner of the use can also be given as a packaging overprint on the medical preparation ready, or can be taken from an information leaflet which can be brought together with medicinal preparations which contain thrombolytically active proteins. As suitable forms of administration for thrombolytically active proteins galenical formulations, for example lyophilisates or solutions in appropriate containers, such as e.g., in ampoules are preferred. As a rule, these formulations contain usual pharmaceutical adjuvants which are suitable for the preparation of isotonic solutions, and may also include additional stabilizing and solubilizing agents.

Thrombolytically active proteins which, in comparison with rt-PA possesses a prolonged half life time, are preferred. These proteins bring about dissolution of thrombi and bring about reperfusion through blood vessels. As already mentioned above, the half life of rt-PA in human blood is about 3–6 minutes.

In accordance with the invention, it is preferred to use thrombolytically active proteins which have a half life at least twice that of rt-PA. In particular, those thrombolytically active proteins which have half lives 3–30 times that of r-tPA are preferred. More particularly, the agent should have a half life 3–7 times, and more preferably 3–5 times that of r-tPA. In terms of minutes, the thrombolytically active proteins should have half lives of from at least about 10 minutes to about 90 minutes, preferably at least about 10 to about 40 minutes, and more preferably about 10–20 minutes.

In the meaning of the present invention, thrombolytically active proteins include, e.g., LY 210825 (K2P from Syrian hamster cell lines, Cir. 1990, 82, 930–940); ΔFE3x and ΔFE1x (K1K2P from Chinese hamster ovary cells, Blood, 1988, 71, 216–219); ΔFEK1 (K2P from mouse C127 cells, J. Cardiovasc. Pharmacol. 1990, 16, 197–209); E-6010 (Jap. Circ. J. 1989, 53, p. 918); t-PA variants (Thromb. Haemost., 1989, 62, p. 542); K2P and D-K2P (Thromb. Haemost., 1989, 62, p. 393); MB-1018 (FK2K2P, Thromb. Haemost., 1989, 62, p. 543); FK2P (FASEB J., 1989, 3, A1031, abstract 4791); Δlx (Circulation, 1988, 4, II-15); K1K2P (Thromb. es., 1988, 50, 33–41); FK1K2P (J. Biol. Chem., 1988, 263, 1599–1602). Especially preferred are thrombolytically active proteins which consists essentially of the K2 ("Kringle 2"), and serine protease ("P") domains of human t-PA. Especially preferred is the thrombolytically active protein of U.S. Pat. No. 5,223,256, the disclosure of which is incorporated by reference and is set forth at SEQ ID NO: 1. Other proteins of this kind are described in the following references:

U.S. Pat. No. 4,970,159; EP-A-0,207,589; AU 61804/86; EP-A-0,231,624; EP-A-0,289,508; JP 63133988; EP-A-0,234,051; EP-A-0,263,172; EP-A-0,241,208; EP-A-0, 292,009; EP-A-0,297,066; EP-A-0,302,456; EP-A-0,379, 890.

In the case of such thrombolytically active proteins with prolonged half life, the pharamcokinetic profile differs from r-tPA. The determination of the half life takes place according to the processes known from the prior art (Pharmacokinetics, Ch. 2, Marcel Dekker, New York 1982 ).

Preferred thrombolytically active proteins include molecules produced by recombinant DNA technology which contain the regions of the natural protein human t-PA responsible for thrombolysis. Those proteins can be used which display deletions or substitutions of individual or several amino acids in the sequence of the molecule as long as the half life of such derivatives is prolonged with regard to rt-PA in the manner described above. Preferred are derivatives which consist essentially of the K2 and P domains of the t-PA.

By way of example for the present invention, thrombolytically active protein K2P (BM 06.022) described in more detail in U.S. Pat. No. 5,223,256, the disclosure of which is incorporated by reference. It consists essentially of the kringle 2(K2) and protease (P) domains of human t-PA and, because of its expression in *Escherichia coli* cells, is unglycosylated. The specific activity of K2P is 550±200 KU/mg. K2P is used for the thrombolytic therapy of thromboembolic disease, such as myocardial infarction, lung embolism, stroke and other occlusive vessel diseases.

Due to lack of glycosylation reduced clearance and a prolonged half life as compared to t-PA by at least the factor 3–4 results. The prolonged half life makes possible the use of the substance in clinically desirable multiple bolus administration. The thrombolytic effect of the bolus administration of the substance was investigated in various animal models. These showed a thrombolytic effectiveness increase of approximately 5 compared with rt-PA. Especially impressive was the rapid opening of thrombolytically occluded vessels, in comparison with rt-PA and other thrombolytics, which means a reduced time for the blood vessel opening in comparison with other thrombolytics and thus a more rapid reperfusion of the infarcted myocardial tissue.

On the basis of the improved pharmacokinetic properties of K2P, the effective dose to be administered can be reduced and K2P can be administered as i.b. multiple bolus injection. A very rapid maximum reperfusion is achieved. Furthermore, by the administration of double or multiple bolus, the impairment of perfusion in the coronary arteries after reperfusion (tendency to reocclude) is significantly reduced or prevented. In addition, after double or multiple boli, the decrease of plasma fibrinogen is smaller than after the single bolus injection of the same total dose.

Besides the rapid opening of thrombolytically occluded blood vessels, the inhibition of the reocclusion of the opened blood vessels is of great clinical importance since a reocclusion of the infarcted blood vessel can lead to clinically important reinfarction with clinical complications resulting therefrom.

The administration of K2P as bolus in equieffective dose in comparison to the infusion of rt-PA leads, in the animal model, to a surprisingly rapid opening of infarcted blood vessels and thus makes possible a rapid reperfusion of infarcted myocardial tissue. In view of the present knowledge regarding thrombolysis, this observed effect is to be evaluated very positively from the clinical point of view.

The time integral between beginning of the first and subsequent bolus injection is indication-dependent and can amount to between 10–90 minutes, 30–90 minutes being specially preferred. The injection period is itself relatively short and amounts, depending upon the volume to be administered, to about 0.5–3 minutes, with an injection rate of about 5–10 ml/min being especially advantageous.

"Multiple bolus administration" refers, e.g., to the cumulated administration of two or more individual bolus injections which are administered over an interval of time. Two or more, preferably three, bolus injections are carried out daily, whereby the therapy can extend over the course of several successive days. This treatment scheme can be interrupted by one or two days so that administration in the form of bolus injections can take place, for example, on every second day during the whole treatment period. Essentially, this cumulated administration of single boli differs from the known single bolus administration in that the administration is repeated daily several times. If the time interval between the first and a subsequently following bolus injection is relatively short, about 10 minutes up to one hour, one speaks of a double bolus or multiple bolus administration. If the time intervals are of the order of magnitude of several hours, then one can also speak of a cumulated administration of single boli.

For the production of the pharmaceutical forms of administration with regard to the thrombolytically active protein, the usual pharmaceutical adjuvants and additive materials can be used. Furthermore, stabilizing or solubilizing agents, such as basic amino acids (arginine, lysine or ornithine) can be used. Suitable galenical forms of administration are known from the prior art or can be produced according to the generally usual methods (cf. U.S. Pat. No. 4,477,043; EP 0,228,862; WO91/08763; WO91/08764; WO91/08765; WO91/08766; WO91/08767 or WO90/01334). The material can be administered in lyophilized form or as an injection solution, ready for use. The bolus injection can take place intravenously, intramuscularly or also subcutaneously. Intravenous injection is preferred.

The amount of the thrombolytically active protein can be the same or also different in the boli, depending upon the particular requirements. As a rule, amounts of 3–50 MU per container are used, corresponding to approximately 5–90 mg of protein. A larger amount of the protein is preferably administered with the first bolus than for the second bolus injection. In particular, amounts of 5–20 MU, especially of 5–15 MU, are used for the first and 3–25 MU, especially 3–10 MU for the second bolus injection. It is especially preferred to use about 10 MU for the first and about 5 MU for the second injection. The cumulative dose preferably lies in the range of 15–40 MU.

The invention is explained in more detail on the basis of the following examples.

Example 1

For the experiments, a dog model was used for the simulation of myocardial infarction. Adult beagles of both sexes were narcotized with barbiturate, intubated and artificially respirated. Arterial and venal catheters were applied in order to monitor the blood pressure, to administer substances or to take blood samples. The chest was opened and the heart exposed. A short segment of the ramus circumflexes of the arterial coronaria sinistra was isolated and prepared. Subsequently, the coronary artery was provided with the following instruments in proximal to distal direction: an electromagnetic flow probe for the measurement of the blood flow in the coronary artery, a stimulation electrode, an adjustable screw and a thread. The tip of the stimulation electrode was passed through the wall of the coronary artery and so placed within the blood vessel that the needle tip came into contact with the inner surface of the blood vessel. The screw was adjusted so that 90% of the reactive hyperemia were eliminated as the result of a short-term interruption of perfusion of the coronary artery.

A thrombus in the coronary artery was formed according to the method originally described in Romson et al. (Thromb. Res., 1980; 17: 841–853) in order to initiate myocardial infarction. The method was employed in the modified form of Shebuski et al. (J. Pharmacol. Exp. Ther. 1988; 246: 790–796). Via the stimulation electrode, a 150 microampere direct current was applied to the coronary artery and maintained until the blood flow in the coronary artery fell to 0 ml/min and remained there for at least three minutes. Subsequently, the thrombus should age for 30 minutes. Over this time period, the animals were heparinized at a dosage of 1000 unites/animal/hour. 30 minutes after thrombus formation, the thrombolytic protein or a solvent was administered as a one-minute i.v. bolus injection to six animals per group. BM 06.022 was administered in four doses: 50, 100, 140 and 200 KU/kg. rt-PA was also given in four doses: 200, 800, 1130 and 1600 KU/kg (=2 mg/kg). The specific activity of rt-PA was 800,000 IU/mg (=800 KU/mg). Plasma samples were obtained before and again after injection of the thrombolytic in order to determine the concentration of the activity of BM 06.022 or of rt-PA according to the method of Verheijen et al. (Thromb. Haemostas. 1982;

48: 266–269). Reperfusion was assumed if at least 33% of the initial blood flow in the coronary artery was again achieved. Accordingly, the time to reperfusion from the beginning of the injection up to the achievement of this blood was defined. In each animal in an additional experimental group, BM 06.022 was administered in a dosage of 140 KU/kg and t-PA in a dosage of 800 KU/kg (=1 mg/kg) intravenously over 90 minutes as continuous infusion (10% of the total dosage as initial i.v. bolus).

Figure 2:
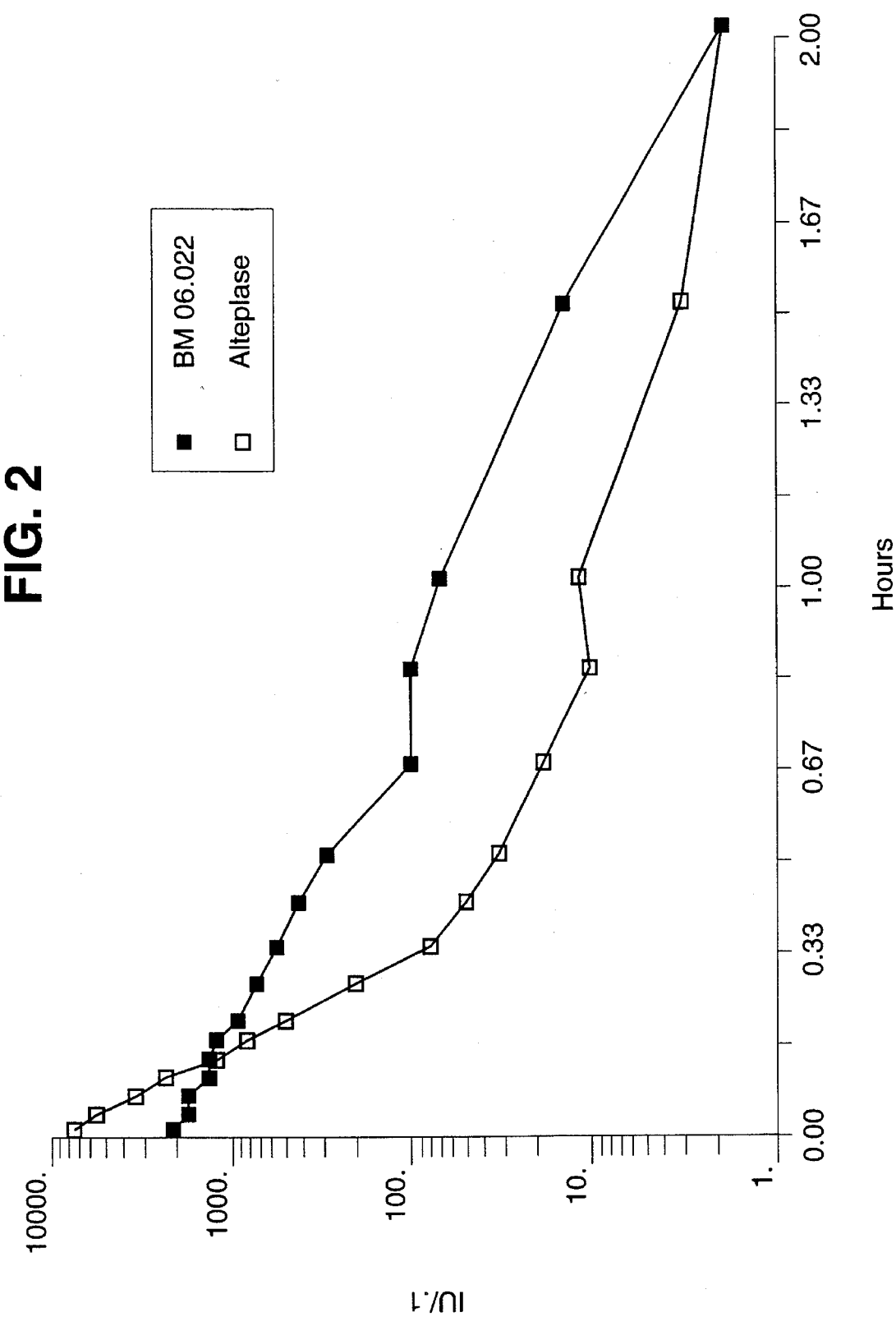
FIG. 2 compares plasma concentration time curves, pharmacokinetically, using BM 06.022 and rt-PA "Alteplase" in anesthetized doges. Either 140 KU/kg (1 mg/kg) of Alteplase were used, in groups of six dogs. What is presented is the arithmetic mean value. Starting concentration was subtracted from subsequent measurements.

FIG. 1 shows the dose-effect relationship for the reperfusion rate after bolus injection of BM 06.022 or of rt-PA. 100% reperfusion (6 out of 6 animals) was achieved with i.v. bolus injection of 200 KU/kg in the case of BM 06.022. In the case of the same dose of rt-PA, none of the animals reperfused. For the achievement of the same maximum effect, an injection of 1600 KU/kg (=2 mg/kg) of rt-PA was necessary. This injection dose is approximately twice as high as the dose of rt-PA presently used in the clinic as infusion (about 1 mg/kg). The higher thrombolytic potency of BM 06.022, as seen by the shift to the left of the dose effect curve, can be explained by the improved phamacokinetic properties of BM 06.022 (see FIG. 2). The total plasma clearance of BM 06.022 amounts to 4.4±0.4 and that of rt-PA to 20.4±2.0 ml/min$^-$1/kg$^{-1}$. Thus the total plasma clearance (a measure of the removal of a substance from the plasma) of BM 06.022 is about 4.6 times slower than that of rt-PA. Furthermore, it was found that rt-PA after infusion, achieves twice as high a reperfusion rate than after single bolus injection of the same dose (800 KU/kg). BM 06.022 in a dose of 140 KU/kg shows the same reperfusion (4 out of 6 animals) after injection and after infusion but the time to reperfusion was significantly shorter than injection (Table 1).

The results show that rt-PA displays more favorable thrombolytic success after infusion than after injection. This finding agrees with the clinical practice in which rt-PA is usually administered as an infusion (Chesebro eta., Circulation, 1987; 76: 142–254). The slower elimination of BM 06.022 in from the plasma as compared to rt-PA led to a higher thrombolytic potency of BM 06.022. Not only is dosage reduction thereby possible but, after single i.v. bolus injection, surprisingly, a more rapid reperfusion takes place than after infusion.

Coronary thrombolytic properties of Alteplase on BM 06.022

|  | dose (kU/kg) | reperfusion rate | time to reperfusion (min) | reocclusion rate | time to reocclusion (min) |
|---|---|---|---|---|---|
| Alteplase bolus injection | 800 | 2/6 | 35 | 1/2 | 4 |
| Alteplase infusion | 800 | 4/6 | 18 ± 8 | 4/4 | 7.8 ± 4.1 |
| BM 06.022 bolus injection | 140 | 4/6 | 15 ± 6 | 4/4 | 9.3 ± 5.3 |
| BM 06.022 infusion | 140 | 4/6 | 59 ± 12$^+$ | 4/4 | 3 ± 0.4 |

The data represent average values ±SEM; n=6 per group +p<0.05 vs. BM 06.022 injection group by means of Mann-Whitney test.

Example 2

For the experiments described herein, the same dog model of coronary artery thrombosis as in Example 1 was used. However, in contrast to the experiments in Example 1, the thrombus was aged for one hour instead of only 30 minutes. BM 06.022, i.e. "K2P" was administered either as a single i.v. bolus administration, the first bolus dose amounted to 140 KU/kg, followed by the second bolus in a dose of 140 or 50 KU/kg of BM 06.022. (44 minutes later). Each of the four experimental group consists of six dogs. Additional parameters for the evaluation where the maximum of the coronary blood flow which was measured after reperfusion and the coronary blood flow at termination of the experiment three hours after injection. Furthermore, the cumulative patency time was calculated; thereunder one understands the sum of the time intervals after reperfusion in which coronary blood flow was present. The animal model is so designed that typically, after reperfusion, cyclic flow variations occur with reocclusion. At the end of the experiment, the residual thrombus was removed and its wet weight measured.

Figure 3:
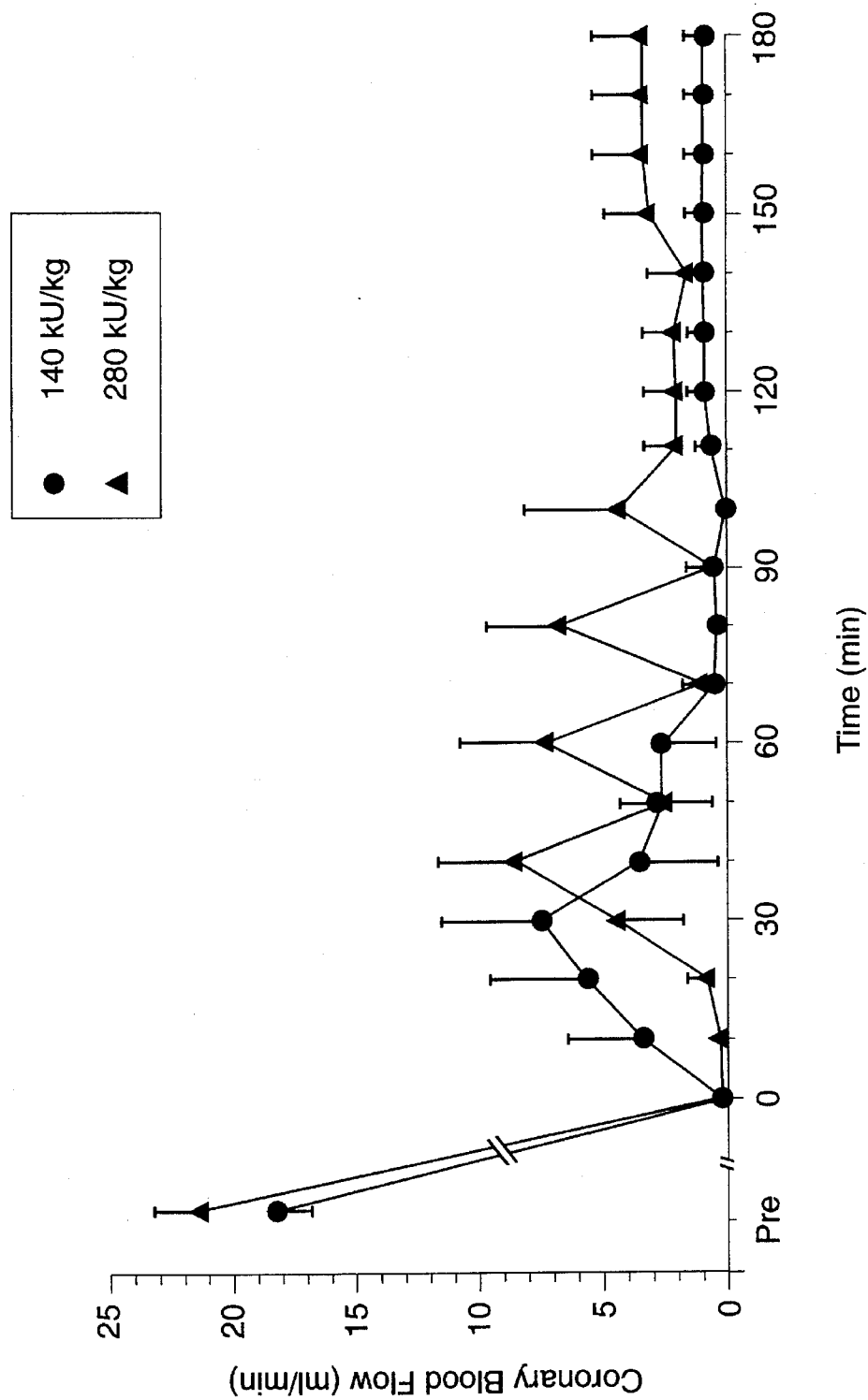
FIG. 3 displays time course of coronary blood flow after a single intravenous bolus injection, using either 140 or 280 KU/kg of BM 06.022, at time point t=0 minutes. Data are shown in mean values ±SEM, where four dogs were used in each group. "Pre" indicates initial blood flow.
Figure 4:
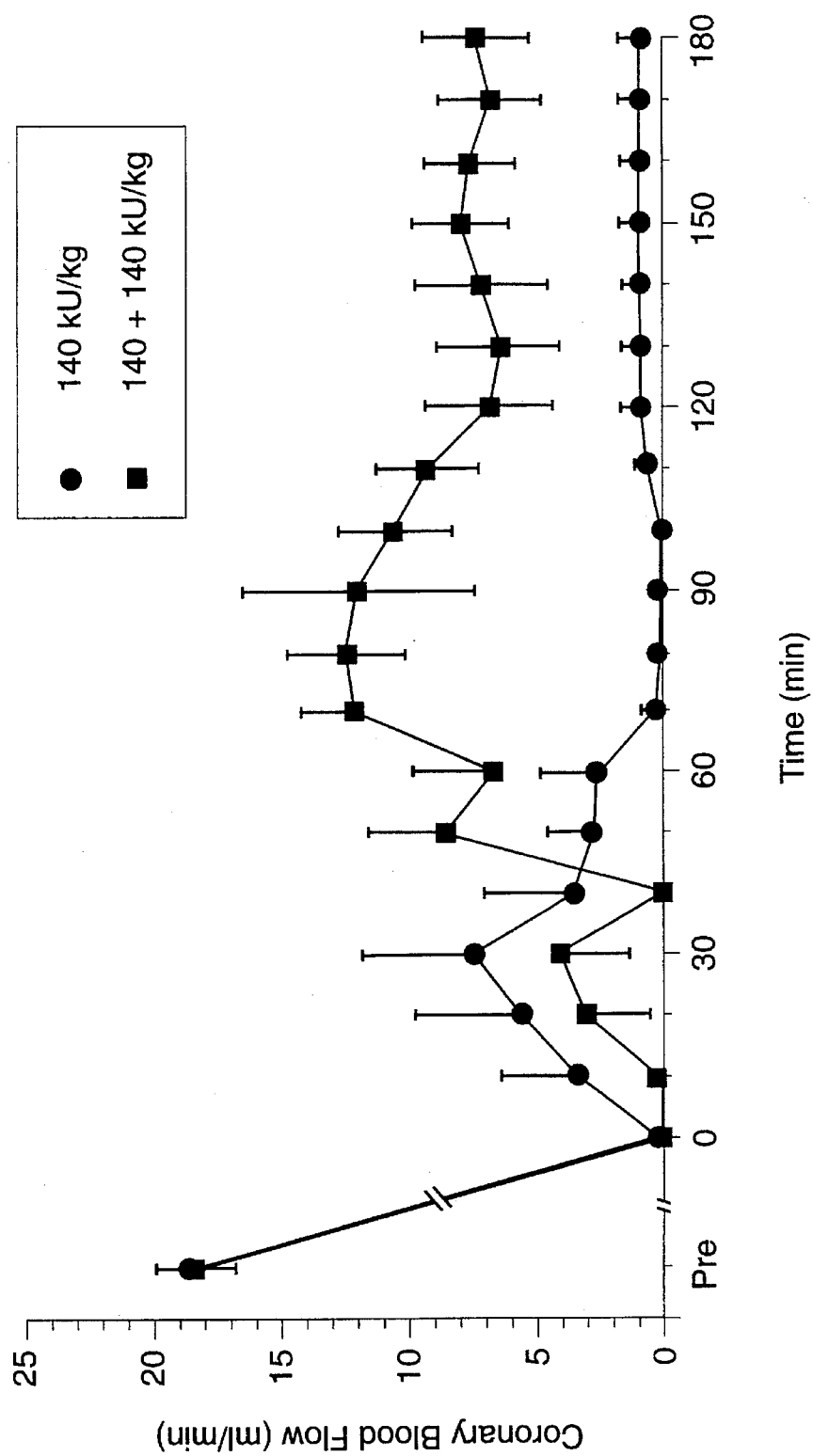
FIG. 4 also shows time course of coronary blood flow as in FIG. 3, (single bolus, t=0), and double bolus (140 KU/kg each bolus, at t=0 and t=44 minutes).
Figure 5:
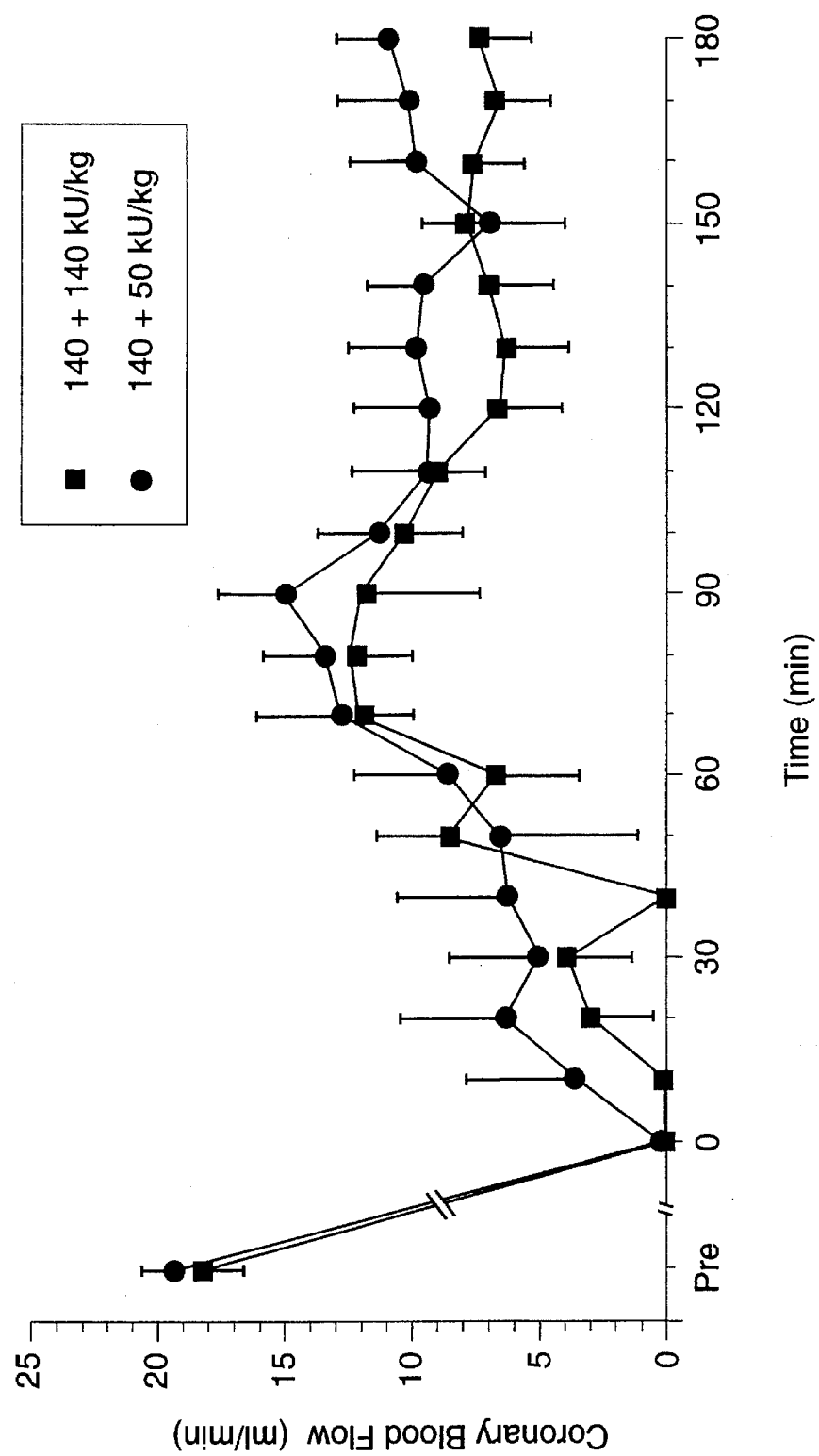
FIG. 5 shows time course of coronary blood flow before and after double bolus administration (140 KU/kg each bolus, for six dogs), or of 140 and 50 KU/kg administrations (for five dogs), of BM 06.022 in both cases, again at t=0 and t=44 minutes. Data are calculated and presented as explained in FIG. 3.

In both groups with single bolus injection, the four of six animals reperfused. In the double bolus group, six of six or five of six animals reperfused (Table 2). The results shown in Table 3 for the cumulative patency time, the coronary blood flow and the residual thrombus weight show that double bolus administration of BM 06.022 significantly increased the coronary blood flow which also remains significantly increased at the end of the experiment, and the residual thrombus weight has decreased significantly in comparison with the single bolus injection of 140 KU/kg. FIG. 3 shows that an increase of the single bolus injection from 140 to 280 KU/kg did not markedly improve the coronary blood flow. Strongly cyclic flow variations were still observed. On the other hand, in FIG. 4 it can be seen that the double bolus administration of 140 and 140 KU/kg of BM 06.022 clearly improved the coronary blood flow in comparison with the single bolus injection of 140 KU/kg of BM 06.022. The same effect on the coronary blood can also be achieved by the double bolus administration of 140 and 50 KU/kg of BM 06.022 (FIG. 5). As Table 4 shows, dividing up a total dose of 280 KU/kg into 140 and 140 KU/kg instead of the single bolus injection of the same total dose of BM 06.022 prevents the significant decrease of the plasma fibrinogen observed previously.

TABLE 2

Reperfusion characteristics on BM 06.022-treated dogs

| BM 06.022 | reperfusion rate (reperfused/all) | | time to reperfusion (min) | |
|---|---|---|---|---|
| dose (kU/kg) | in all | after the 2nd bolus | after the 1st bolus | after the 2nd bolus |
| 140 | 4/6 | — | 18.3 ± 6.0 | — |
| 280 | 4/6 | — | 26.5 ± 4.9 | — |
| 140 + 140 | 6/6 | 2/6 | 21.8 ± 4.4 | 16.0, 4.0 |
| 140 + 50 | 5/6 | 1/6 | 18.3 ± 4.1 | 8.0 |

The data represent mean values ±SEM or frequency data 1st bolus: t=0–1 min; 2nd bolus: t=44–45 min.

TABLE 3

Characteristics of the coronary blood flow after reperfusion and thrombus weight in BM 06.022-treated dogs

| BM 06.022 dosing (kU/mg) | N | cumulative patency time (min) | coronary blood flow (ml/min) maximum | coronary blood flow (ml/min) at 3 h | residual thrombus moist wet (mg) |
|---|---|---|---|---|---|
| 14C | 4 | 47.5 ± 13.1 | 12.5 ± 3.2 | 0.8 ± 0.8 | 6.1 ± 1.1 |
| 28C | 4 | 80.8 ± 34.1 | 11.8 ± 1.8 | 3.3 ± 1.9 | 3.5 ± 0.8+ |
| 140 + 140 | 6 | 121.5 ± 11.2+ | 19.3 ± 1.5+ | 6.8 ± 1.8+ | 2.4 ± 0.8+ |
| 140 + 50 | 5 | 127.4 ± 10.3+ | 21.2 ± 2.2+ | 8.4 ± 1.7+ | 3.4 ± 0.5+ |

The data represent the mean value±SEM; n=6/group for the thrombus weight. Cumulative patency time: sum of the time intervals in which the coronary artery was open (determined via measurement of the coronary blood flow) +p<0.05 vs. the 140 kU/kg BM 06.022 group by means of Student's t-test.

TABLE 4

Coagulation variables in BM 06.022-treated dogs

| BM 06.022 dose (kU/kg) | residual fibrinogen (% of the initial value) | residual plasminogen (% of the initial value) | residual $\alpha_2$-antiplasmin (% of the initial value) |
|---|---|---|---|
| 140 | 95.7 ± 3.7 | 90.7 ± 3.6+ | 52.2 ± 6.5 |
| 280 | 74.0 ± 9.4+ | 76.0 ± 2.4+ | 54.5 ± 19.3 |
| 140 + 140 | 97.5 ± 6.0 | 82.5 ± 2.4+ | 60.2 ± 7.5 |
| 140 + 50 | 94.9 ± 3.5 | 82.6 ± 2.9+ | 62.0 ± 14.1 |

The data represent the mean value n=6/group The coagulation variables are represented as the 2-hour percentage values of the initial value +p<0.05 vs. the 140 kU/kg BM 06.022 group by means of Student's t-test.

The results show that the deterioration of the coronary blood flow after reperfusion, which, in this model, intrinsically occurs in simulation of patients with reocclusion tendency, cannot be prevented by single bolus injection, even at higher dosages. On the single hand, the administration of the double bolus is surprisingly able to prolong the cumulative patency time, to increase the blood flow quantitatively and to maintain the increased flow up to the end of the experiment. In addition, the double bolus injection has the surprisingly advantage of a lower decrease of the plasma fibrinogen in contrast to the single bolus injection of the same total dosage. The size of the second bolus in the double bolus administration can thereby be made variable without limiting the success.

It will be understood that the specification and examples are illustrative but not limitative of the present invention and that other embodiments within the spirit and scope of the invention will suggest themselves to those skilled in the art.

We claim:

1. Method for treatment of a thromboembolic condition, comprising administering to a subject with a thromboembolic condition an amount of a thrombolytically active protein consisting of SEQ ID NO: 1, wherein said thrombolytically active protein is administered in an amount sufficient to prevent reocclusion, and is administered in the form of two or more boli.

2. The method of claim 1, wherein said thrombolytically active protein is administered in a dose of from 3–50 MU per bolus.

3. The method of claim 1, comprising administering said two or more boli at an interval of from 10 minutes to 90 minutes therebetween.

4. The method of claim 1, comprising administering a first bolus of said thrombolytically active protein at a dose of from 5–20 MU, and a second bolus of said thrombolytically active protein at a dose of 3–15 MU.

5. The method of claim 1, wherein said thromboembolic condition is myocardial infarct, a lung embolism, a brain stroke, or an occlusive disease of the circulatory system.

6. The method of claim 1, further comprising administering an amount of heparin to said subject together with said thrombolytically active protein.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 355 amino acids
        ( B ) TYPE: amino acids
        ( C ) TOPOLOGY: linear ( x i ) SEQUENCE DESCRIPTION: SEQ ID NO: 1:

```
Ser  Tyr  Gln  Gly  Asn  Ser  Asp  Cys  Tyr  Phe  Gly  Asn  Gly  Ser  Ala  Tyr
                    5                        10                       15

Arg  Gly  Thr  His  Ser  Leu  Thr  Glu  Ser  Gly  Ala  Ser  Cys  Leu  Pro  Trp
               20                       25                       30

Asn  Ser  Met  Ile  Leu  Ile  Gly  Lys  Val  Tyr  Thr  Ala  Gln  Asn  Pro  Ser
               35                       40                       45

Ala  Gln  Ala  Leu  Gly  Leu  Gly  Lys  His  Asn  Tyr  Cys  Arg  Asn  Pro  Asp
     50                       55                       60

Gly  Asp  Ala  Lys  Pro  Trp  Cys  His  Val  Leu  Lys  Asn  Arg  Arg  Leu  Thr
65                       70                       75                       80

Trp  Glu  Tyr  Cys  Asp  Val  Pro  Ser  Cys  Ser  Thr  Cys  Gly  Leu  Arg  Gln
                    85                       90                       95
```

| | | | | | | | | | | | | | | |
|---|---|---|---|---|---|---|---|---|---|---|---|---|---|---|
| Tyr | Ser | Gln | Pro<br>100 | Gln | Phe | Arg | Ile | Lys<br>105 | Gly | Gly | Leu | Phe | Ala<br>110 | Asp | Ile |
| Ala | Ser | His<br>115 | Pro | Trp | Gln | Ala | Ala<br>120 | Ile | Phe | Ala | Lys | His<br>125 | Arg | Arg | Ser |
| Pro | Gly<br>130 | Glu | Arg | Phe | Leu | Cys<br>135 | Gly | Gly | Ile | Leu | Ile<br>140 | Ser | Ser | Cys | Trp |
| Ile<br>145 | Leu | Ser | Ala | Ala | His<br>150 | Cys | Phe | Gln | Glu | Arg<br>155 | Phe | Pro | Pro | His | His<br>160 |
| Leu | Thr | Val | Ile | Leu<br>165 | Gly | Arg | Thr | Tyr | Arg<br>170 | Val | Val | Pro | Gly | Glu<br>175 | Glu |
| Glu | Gln | Lys | Phe<br>180 | Glu | Val | Glu | Lys | Tyr<br>185 | Ile | Val | His | Lys | Glu<br>190 | Phe | Asp |
| Asp | Asp | Thr<br>195 | Tyr | Asp | Asn | Asp | Ile<br>200 | Ala | Leu | Leu | Gln | Leu<br>205 | Lys | Ser | Asp |
| Ser | Ser | Arg<br>210 | Cys | Ala | Gln | Glu<br>215 | Ser | Ser | Val | Val | Arg<br>220 | Thr | Val | Cys | Leu |
| Pro<br>225 | Pro | Ala | Asp | Leu | Gln<br>230 | Leu | Pro | Asp | Trp | Thr<br>235 | Glu | Cys | Glu | Leu | Ser<br>240 |
| Gly | Tyr | Gly | Lys | His<br>245 | Glu | Ala | Leu | Ser | Pro<br>250 | Phe | Tyr | Ser | Glu | Arg<br>255 | Leu |
| Lys | Glu | Ala | His | Val<br>260 | Arg | Leu | Tyr | Pro<br>265 | Ser | Ser | Arg | Cys | Thr<br>270 | Ser | Gln |
| His | Leu | Leu<br>275 | Asn | Arg | Thr | Val<br>280 | Thr | Asp | Asn | Met | Leu<br>285 | Cys | Ala | Gly | Asp |
| Thr | Arg<br>290 | Ser | Gly | Gly | Pro<br>295 | Gln | Ala | Asn | Leu | His<br>300 | Asp | Ala | Cys | Gln | Gly |
| Asp<br>305 | Ser | Gly | Gly | Pro | Leu<br>310 | Val | Cys | Leu | Asn | Asp<br>315 | Gly | Arg | Met | Thr | Leu<br>320 |
| Val | Gly | Ile | Ile | Ser<br>325 | Trp | Gly | Leu | Gly | Cys<br>330 | Gly | Gln | Lys | Asp | Val<br>335 | Pro |
| Gly | Val | Tyr | Thr<br>340 | Lys | Val | Thr | Asn | Tyr<br>345 | Leu | Asp | Trp | Ile | Arg<br>350 | Asp | Asn |
| Met | Arg | Pro | | | | | | | | | | | | | |

(2) INFORMATION FOR SEQ ID NO: 2:

(i) SEQUENCE CHARACTERISTICS:
        (A) LENGTH: 1068 nucleotide bases
        (B) TYPE: nucleic acid
        (C) STRANDEDNESS: double
        (D) TOPOLOGY: linear (xi) SEQUENCE DESCRIPTION: SEQ ID NO: 2:

```
ATGTCTTACC AAGGAAACAG TGACTGCTAC TTTGGGAATG GGTCAGCCTA CCGTGGCACG    60
CACAGCCTCA CCGAGTCGGG TGCCTCCTGC CTCCCGTGGA ATTCCATGAT CCTGATAGGC   120
AAGGTTTACA CAGCACAGAA CCCCAGTGCC CAGGCACTGG GCCTGGGCAA ACATAATTAC   180
TGCCGGAATC CTGATGGGGA TGCCAAGCCC TGGTGCCACG TGCTGAAGAA CCGCAGGCTG   240
ACGTGGGAGT ACTGTGATGT GCCCTCCTGC TCCACCTGCG GCCTGAGACA GTACAGCCAG   300
CCTCAGTTTC GCATCAAAGG AGGGCTCTTC GCCGACATCG CCTCCCACCC CTGGCAGGCT   360
GCCATCTTTG CCAAGCACAG GAGGTCGCCC GGAGAGCGGT TCCTGTGCGG GGGCATACTC   420
ATCAGCTCCT GCTGGATTCT CTCTGCCGCC CACTGCTTCC AGGAGAGGTT TCCGCCCCAC   480
CACCTGACGG TGATCTTGGG CAGAACATAC CGGGTGGTCC CTGGCGAGGA GGAGCAGAAA   540
TTTGAAGTCG AAAAATACAT TGTCCATAAG GAATTCGATG ATGACACTTA CGACAATGAC   600
```

| | | | | | | |
|---|---|---|---|---|---|---|
| ATTGCGCTGC | TGCAGCTGAA | ATCGGATTCG | TCCCGCTGTG | CCCAGGAGAG | CAGCGTGGTC | 660 |
| CGCACTGTGT | GCCTTCCCCC | GGCGGACCTG | CAGCTGCCGG | ACTGGACGGA | GTGTGAGCTC | 720 |
| TCCGGCTACG | GCAAGCATGA | GGCCTTGTCT | CCTTTCTATT | CGGAGCGGCT | GAAGGAGGCT | 780 |
| CATGTCAGAC | TGTACCCATC | CAGCCGCTGC | ACATCACAAC | ATTTACTTAA | CAGAACAGTC | 840 |
| ACCGACAACA | TGCTGTGTGC | TGGAGACACT | CGGAGCGGCG | GGCCCAGGC | AAACTTGCAC | 900 |
| GACGCCTGCC | AGGGCGATTC | GGGAGGCCCC | CTGGTGTGTC | TGAACGATGG | CCGCATGACT | 960 |
| TTGGTGGGCA | TCATCAGCTG | GGGCCTGGGC | TGTGGACAGA | AGGATGTCCC | GGGTGTGTAC | 1020 |
| ACAAAGGTTA | CCAACTACCT | AGACTGGATT | CGTGACAACA | TGCGACCG | | 1068 |